United States Patent [19]

Yamaguchi et al.

[11] Patent Number: 4,929,797

[45] Date of Patent: May 29, 1990

[54] METHOD FOR PRODUCING HYDROCARBONS HAVING TWO CARBON ATOMS

[75] Inventors: Tatsuaki Yamaguchi, Tokyo; Kozo Hirota, Chiba, both of Japan

[73] Assignee: Mitsubishi Kasei Corporation, Tokyo, Japan

[21] Appl. No.: 270,638

[22] Filed: Nov. 14, 1988

[30] Foreign Application Priority Data

Nov. 14, 1987 [JP] Japan .................. 62-287656

[51] Int. Cl.$^5$ .............................. C07C 2/00
[52] U.S. Cl. ................................ 585/921; 585/636; 585/650; 585/652; 585/926; 585/943
[58] Field of Search ............... 585/636, 650, 652, 943, 585/921, 926

[56] References Cited

U.S. PATENT DOCUMENTS

| | | | |
|---|---|---|---|
| 1,905,520 | 4/1933 | Steigerwald | 585/943 |
| 2,061,597 | 11/1936 | Smith et al. | 585/943 |
| 3,018,309 | 1/1962 | Krejci | 585/652 |
| 4,672,142 | 6/1987 | Green et al. | 585/652 |

FOREIGN PATENT DOCUMENTS 236375  6/1959  Australia .................. 585/652

Primary Examiner—Asok Pal
Attorney, Agent, or Firm—Oblon, Spivak, McClelland, Maier & Neustadt

[57] ABSTRACT

A method for producing hydrocarbons having two carbon atoms, which comprises introducing methane gas into a reactor downwardly from the top, the reactor comprising a pair of reactor walls extending vertically and facing each other, one of the walls being maintained at a high temperature and the other being maintained at a low temperature, so that the methane gas is dimerized primarily through the dehydrogenation on the surface of the high temperature wall to form $C_2$ hydrocarbons and hydrogen, and the $C_2$ hydrocarbons are preferentially diffused and transferred to the low temperature wall side by thermal diffusion effects.

4 Claims, 5 Drawing Sheets

METHOD FOR PRODUCING HYDROCARBONS HAVING TWO CARBON ATOMS

BACKGROUND OF THE INVENTION

1. Field of the Invention

The present invention relates to a method for producing hydrocarbons having two carbon atoms (hereinafter referred to as $C_2$ hydrocarbons) such as ethane, ethylene or acetylene by dihydrogenative coupling of methane.

2. Discussion of Background

A $C_2$ hydrocarbon, particularly ethylene, is the most important substance used as a base material for petrochemical processes presently available, and a number of products are produced therefrom. As is well known, at present, ethylene is produced in a large amount from petroleum as the starting material. Recently, an attention has been drawn to utilization of natural gas as the starting material for chemical industry, in connection with a problem of exhaustion of petroleum resources. There have been attempts by various sectors to change the starting material and to produce ethylene by catalytically oxidizing and dehydrating natural gas i.e. methane. If ethylene can efficiently be synthesized from methane as the main component of natural gas, it can be used directly to the petrochemical processes presently available, whereby the petroleum resources can be saved. Thus, the impact to the chemical industry will be substantial.

With such an object, a method has been studied wherein a gas mixture of methane and oxygen is used as the starting material, and methane is subjected to oxidative coupling by means of various catalysts or without using a catalyst to produce $C_2$ hydrocarbons. For example, an oxidative coupling method by Epson Company is known (Japanese Unexamined Patent Publication No. 01607/1985).

The oxidative coupling reaction as disclosed in the above publication is an exothermic reaction and thus has a merit that the reaction temperature is relatively low. However, it has demerits that the yield of the $C_2$ hydrocarbons and the selectivity for ethylene are low, and water produced as a by-product has no substantial value.

SUMMARY OF THE INVENTION

It is an object of the present invention to solve such problems and to provide a method for producing $C_2$ hydrocarbons, which are capable of improving the yield of the $C_2$ hydrocarbons.

The present invention provides a method for producing hydrocarbons having two carbon atoms, which comprises introducing methane gas into a reactor downwardly from the top, the reactor comprising a pair of reactor walls extending vertically and facing each other, one of the walls being maintained at a high temperature and the other being maintained at a low temperature, so that the methane gas is dimerized primarily by dehydrogenation on the surface of the high temperature wall to form $C_2$ hydrocarbons and hydrogen, and the $C_2$ hydrocarbons are preferentially diffused and transferred to the low temperature wall side by thermal diffusion effects, and withdrawing them from the bottom of the reactor.

In the present invention, methane gas is introduced into a reactor downwardly from the top of the reactor comprising a pair of reactor walls extending vertically and facing each other, one of said walls being maintained at a high temperature and the other being maintained at a low temperature. The methane gas undergoes dehydrogenative coupling reactions, such as reactions as shown below, by the heat from the surface of the high temperature reactor wall to form $C_2$ hydrocarbons (gas) and hydrogen (gas):

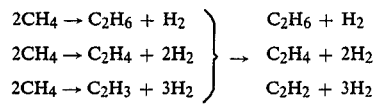

The $C_2$ hydrocarbons are diffused and transferred to the low temperature wall side preferentially to methane and hydrogen and discends to the bottom of the reactor by the downward flow created by the introduction of methane gas. If the $C_2$ hydrocarbons are brought in contact again with the surface of the high temperature wall, further polymerization is likely to proceed to produce oily substance. However, the flow of the methane gas is downward, which is the same direction as the natural flow of the $C_2$ hydrocarbons, whereby the turbulence of the flow in the reactor is very little. Accordingly, the proportion of the $C_2$ hydrocarbons which are in contact with the surface of the high temperature reactor wall is small, and no substantial formation of oily substance will be observed. On the other hand, hydrogen discends to the bottom of the reactor along the high temperature reactor wall, as it is forced to flow by the above downward flow by thermal diffusion effects. Thus, the $C_2$ hydrocarbons and hydrogen are withdrawn from the bottom of the reactor.

DETAILED DESCRIPTION OF THE PREFERRED EMBODIMENTS

The temperature of the high temperature wall is required to be at least a temperature at which the $C_2$ hydrocarbons are readily formed by the dehydrogenative coupling reaction. An optimum temperature is determined taking the relation between the yield and the selectivity for the $C_2$ hydrocarbons into consideration. However, the surface temperature of the high temperature wall is usually within a range of from 900° to 1,500° C., preferebly from 1,000° to 1,400° C.

If the methane gas was introduced upwardly from the bottom of the reactor, the formed $C_2$ hydrocarbons are hardly discharged from the outlet at the top without disturbing thermal diffusion, and it is likely to contact again with the high temperature wall, whereby the thermal polymerization reaction further proceeds to produce an increased amount of oily substance.

As the reactor, there may be employed one wherein a pair of flat plates are disposed to face each other, and one of them is maintained at a high temperature and the other is maintained at a low temperature, one which is composed of two concentric cylinders, or one having such a concentric structure with the inner cylinder replaced by an electrically conductive rod or wire so that it can be heated directly by conducting an electric current.

The surface temperature of the low temperature wall is maintained usually within a range of from 0° to about 300° C., preferably from an ambient temperature to about 200° C.

Now, the present invention will be described in detail with reference to a specific embodiment. However, it should be understood that the present invention is by no means restricted by such a specific embodiment.

(1) Reactor

Figure 1:
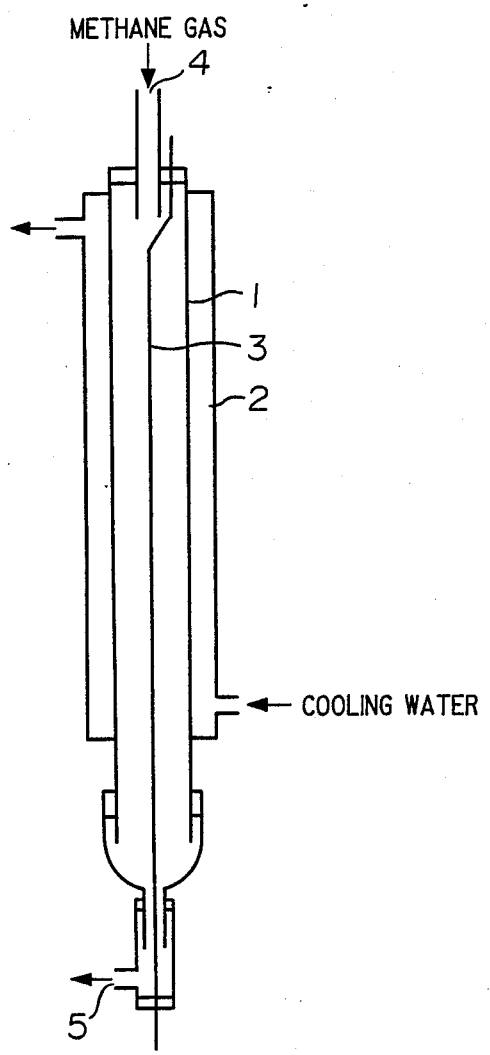
FIG. 1 is a cross-sectional view of an apparatus adapted to carry out the method of the present invention.

FIG. 1 is a view illustrating a reactor used for a test. Reference numeral 1 designates a cylinder made of pyrex glass having a length of 1 m and a diameter of 2 cm and provided externally with a cooling water path 2. At the center of this cylinder 1, a tungsten wire 3 having a length of 70 cm and a diameter of 0.5 mm is vertically disposed. Reference numerals 4 and 5 designate a methane gas inlet and a gas outlet, respectively.

Figure 2:
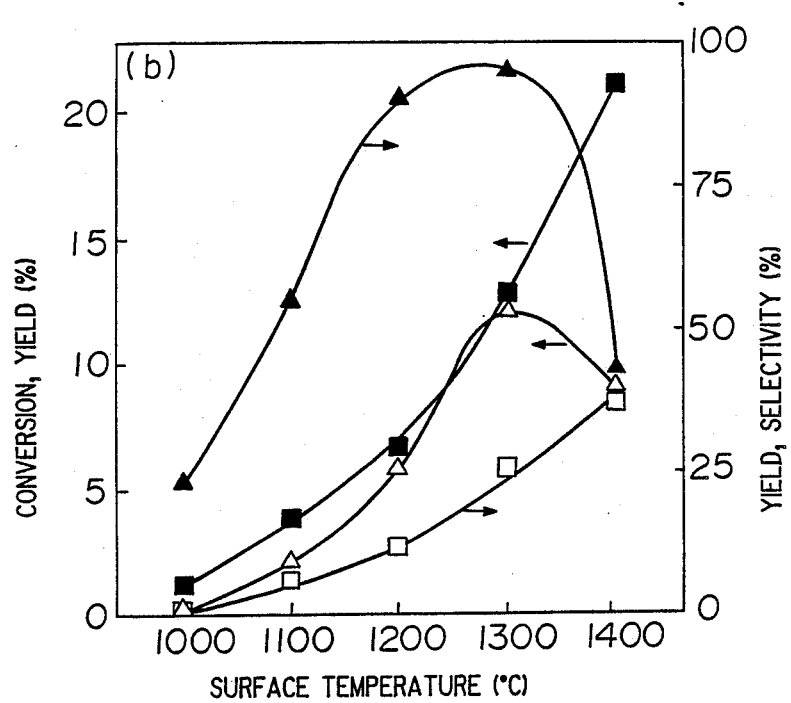
FIGS. 2 and 3 are graphs showing, respectively, the relations between the surface temperature and the yield, etc.

(2) Test for the influence of the surface temperature (i) By using the apparatus as shown in FIG. 1, methane gas was introduced downwardly from the inlet 4 at the top of the reactor 1 at a flow rate of the downflow of 3.82 m/hr. The temperature of the wire 3 was changed to levels of 1,000° C., 1,100° C., 1,200° C. and 1,300° C. The gasses withdrawn from the outlet 5 under the respective temperature conditions were analyzed, respectively, by gas chromatography to determine the conversion of methane, the selectivity and the yield of the $C_2$ hydrocarbons and the yield of hydrogen. The results are shown in FIG. 2, wherein ■ indicates the conversion of methane, ▲ indicates the selectivity for the $C_2$ hydrocarbons, △ indicates the yield of the $C_2$ hydrocarbons, and □ indicates the yield of hydrogen.

Figure 3:
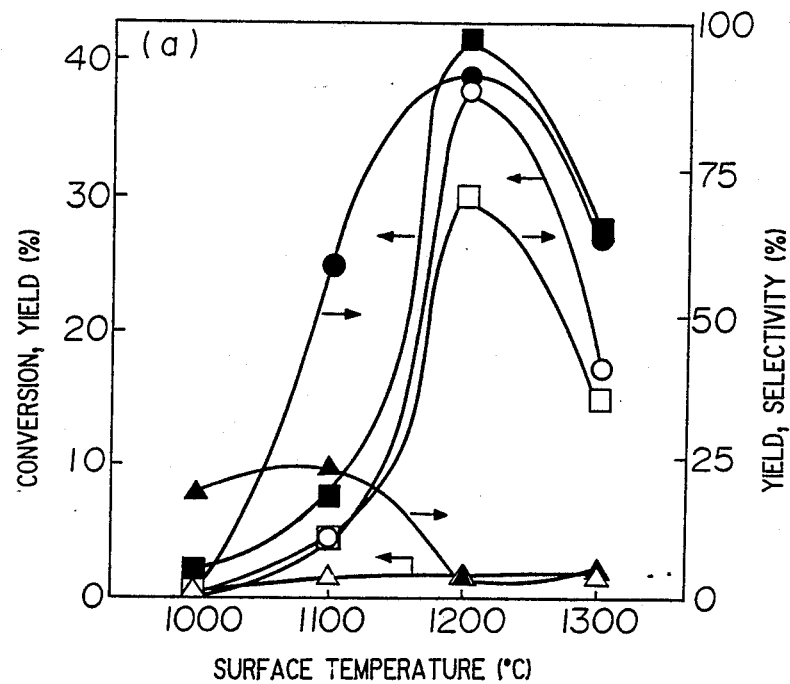

(ii) Whereas the conversion of methane, the selectivity and the yield of the $C_2$ hydrocarbons and the yield of hydrogen were examined in the same manner as in the above step (i) except that by using the same apparatus as shown in FIG. 1, methane gas was introduced upwardly from the bottom and the gasses withdrawn from the top were analyzed. In this case, oily substance was formed. Such substance was withdrawn from the bottom of the reactor, and the selectivity and the yield thereof were examined. The results are shown in FIG. 3, wherein ● indicates the selectivity for the oily substance, and ○ indicates the yield of the oily substance.

Figure 4:
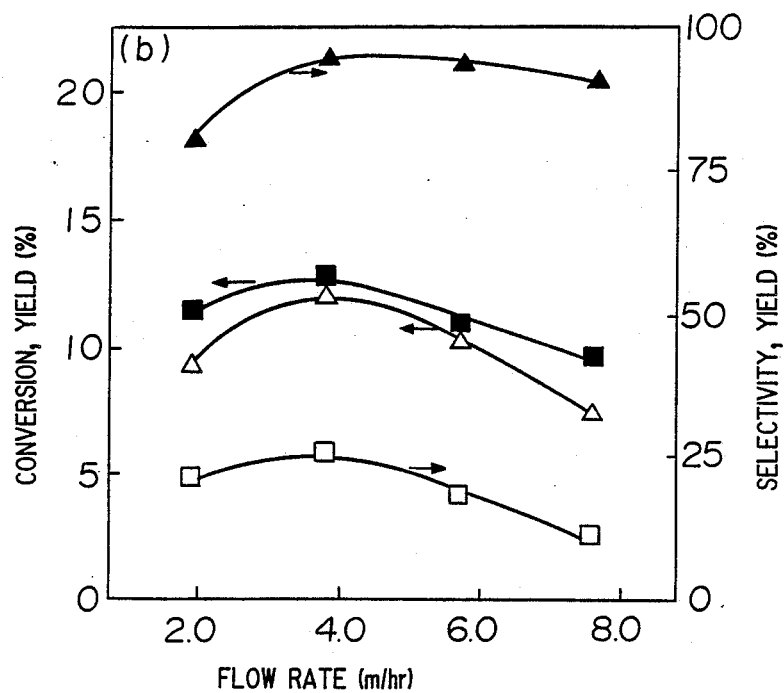
FIGS. 4 and 5 are graphs showing, respectively, the relations between the flow rate and the yield, etc.

(3) Test for the influence of the gas flow rate (i) By using the apparatus of FIG. 1, methane gas was introduced downwardly from the inlet 4 at the top of the reactor 1 while maintaining the temperature of the wire at a level of 1,300° C., and the flow rate was changed to levels of 2.0 m/hr, 4.0 m/hr, 6.0 m/hr and 8.0 m/hr. The gasses withdrawn from the outlet 5 at the respective flow rates were subjected to the same measurements as in the above step (2) (i). The results are shown in FIG. 4.

Figure 5:
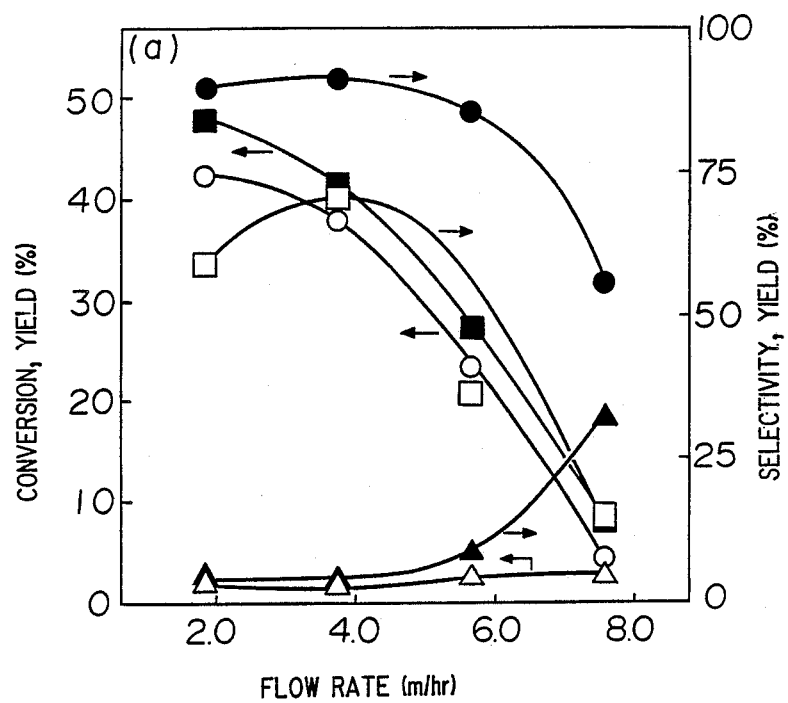

(2) Whereas, the same measurements as in the above step (2) (ii) were conducted in the same manner as in the above step (i) except that by using the same apparatus as shown in FIG. 1, methane gas was introduced upwardly from the bottom, and gasses withdrawn from the top were analyzed. The results are shown in FIG. 5.

(4) Discussion

It is evident from the above results that when methane is introduced from the top, the yield of the $C_2$ hydrocarbons increases with an increase of the surface temperature and shows the maximum value at 1,300° C. At such a temperature level, the yield is as high as at least 10%. At a higher temperature, the conversion of methane increases, and the yield of hydrogen improves, but the formation of carbonaceous substance takes place, and both the selectivity and the yield of the $C_2$ hydrocarbons decrease. The composition of the $C_2$ hydrocarbons is substantially affected by the surface temperature of the tungsten wire. At 1,000° C., ethane constitutes 70%; at from 1,200° to 1,300° C., ethylene constitutes about 95%; and at 1,400° C., acethylene constitutes about 60%. This is due to the fact that the optimum free energy levels in the reactions for the formation of the respective components are different depending upon the temperature.

On the other hand, in the case where methane is introduced from the bottom, the selectivity for oily substance tends to be substantial at a temperature exceeding 1,100° C., and it is as high as about 90% at 1,300° C., whereby the yield of the oily substance is substantial, whereas no substantial formation of such oily substance is observed when methane is introduced from the top. Accordingly, when the methane gas is introduced from the bottom, the yield of the $C_2$ hydrocarbons is far smaller than the case where the methane gas is introduced from the top. From the results of the change of the flow rate, the yield of the $C_2$ hydrocarbons is as high as about 10% within the flow rate range of from 2.0 to 6.0 m/hr when the methane is introduced from the above. Whereas, when methane is introduced from the bottom, the selectivity for the oily substance is high, and the yield of the $C_2$ hydrocarbons is as low as at most 5% generally, although it tends to increase with an increase of the flow rate. Such a difference is believed to be attributalbe to the fact that in the case where the flow of methane gas is directed downwards, the progress of the thermal polymerization reaction can be controlled, but in a case where the flow is directed upwards, the thermal polymerization reaction of the $C_2$ hydrocarbons proceeds.

In the above embodiment, the tungsten wire forming the high temperature reactor wall may be in the form of a coil extending in a vertical direction or in the form of letter U with its curved portion located below, instead of the linear wire as used in the above embodiment. In such a manner, the contact efficiency with the heating surface can be improved, whereby the yield of the $C_2$ hydrocarbons will be improved.

According to the present invention, methane gas is dimerized by dehydrogenation to form the $C_2$ hydrocarbons and hydrogen, and these gasses are separated by thermal diffusion effects and discharged along the downward flow from the bottom of the reactor, whereby the progress of the thermal polymerization reaction of the $C_2$ hydrocarbons is suppressed, and the $C_2$ hydrocarbons can be obtained in high yield and selectivity. Further, by controlling the heating temperature, it is possible to increase the proportion of ethylene useful particularly for the petrochemical industry. Further, the method of the present invention utilizes a dehydrogenative coupling reaction without using oxygen. The by-product is hydrogen which is useful as opposed to useless water in the product of the oxidative coupling process. According to the present invention, separation by thermal diffusion and methane conversion to $C_2$ hydrocarbons take place in the reactor. Therefore, if the gas flow along with the high temperature wall and the one along with the low temperature wall are withdrawn separately, for example by putting a separation wall at the bottom of the reactor, the products of $C_2$ hydrocarbons and at least hydrogen are separately obtained in fairly pure state. Thus, the method of the present invention is economically advantageous.

What is claimed is:

1. A method for producing hydrocarbons having two carbon atoms, which comprises introducing methane gas into a reactor downwardly from the top, said reactor comprising a pair of reactor walls extending vertically and facing each other, one of said walls being maintained at a high temperature and the other being maintained at a low temperature, so that the methane gas is dimerized primarily through the dehydrogenation on the surface of the high temperature wall to form $C_2$ hydrocarbons and hydrogen, and the $C_2$ hydrocarbons are preferentially diffused and transferred to the low temperature wall side by thermal diffusion effects.

2. The method according to claim 1, wherein the high temperature wall has a surface temperature of from 900° to 1,500° C.

3. The method according to claim 1, wherein the low temperature wall has a surface temperature of from 0° to about 300° C.

4. The method according to claim 1, wherein the methane gas is supplied at a flow rate of from 2.0 to 12.0 m/hr.

* * * * *